United States Patent
Kusuzawa

[11] Patent Number: 5,822,062
[45] Date of Patent: Oct. 13, 1998

[54] PARTICLE ANALYZER INCLUDING A ROD LENS HAVING A CURVED SURFACE

[75] Inventor: Hideo Kusuzawa, Kobe, Japan

[73] Assignee: Toa Medical Electronics Co., Ltd., Hyogo, Japan

[21] Appl. No.: 713,638

[22] Filed: Sep. 13, 1996

[30] Foreign Application Priority Data

Sep. 14, 1995 [JP] Japan .................................. 7-236797

[51] Int. Cl.⁶ .................................................. G01N 21/00
[52] U.S. Cl. ........................... 356/343; 356/338; 356/339
[58] Field of Search ..................................... 356/338, 393

[56] References Cited

U.S. PATENT DOCUMENTS

| | | | |
|---|---|---|---|
| 4,577,110 | 3/1986 | MacBride et al. | 356/417 |
| 4,847,734 | 7/1989 | Katoh et al. | 362/32 |
| 5,054,902 | 10/1991 | King | 359/589 |
| 5,140,464 | 8/1992 | Kyogoku et al. | 359/589 |
| 5,173,800 | 12/1992 | King | 359/589 |
| 5,188,092 | 2/1993 | White | 359/435 |
| 5,237,386 | 8/1993 | Harley | 356/338 |

FOREIGN PATENT DOCUMENTS

| | | |
|---|---|---|
| 57-186732 | 11/1982 | Japan . |
| 60-262041 | 12/1985 | Japan . |
| 61-35333 | 2/1986 | Japan . |

*Primary Examiner*—Frank G. Font
*Assistant Examiner*—Jason D. Vierra-Eisenberg

[57] ABSTRACT

A particle analyzer which can maintain optical characteristics of an optical system which is one component thereof at a fixed level for a long period of time is provided. In the particle analyzer comprising a flow cell for forming a sheathed sample flow containing particulate components; an irradiating optical system for irradiating a sheathed sample flow formed in the flow cell; and a light receiving optical system for receiving light emitted from the sheathed sample flow in the flow cell irradiated by the irradiating optical system, the light receiving optical system comprises a rod lens to which the light emitted from the sheathed sample flow in the flow cell enters and an entrance surface of the rod lens is curved.

17 Claims, 9 Drawing Sheets

VERTICAL AXIS 1V/DIV   HORIZONTAL AXIS 2μsec/DIV

FIG. 9

VERTICAL AXIS 1V/DIV   HORIZONTAL AXIS 2μsec/DIV

PARTICLE ANALYZER INCLUDING A ROD LENS HAVING A CURVED SURFACE

BACKGROUND OF THE INVENTION

1. Field of the Invention

The present invention relates to a particle analyzer and more particularly to a particle analyzer for measuring the size, shape, property or the like of particles within a sample containing particulate components such as blood corpuscles and various cells by forming the sample into a sheathed sample flow in a flow cell and by irradiating the sheathed sample flow to measure scattered light and fluorescent light emitted from the sheathed sample flow.

2. Description of Related Art

Figure 7:
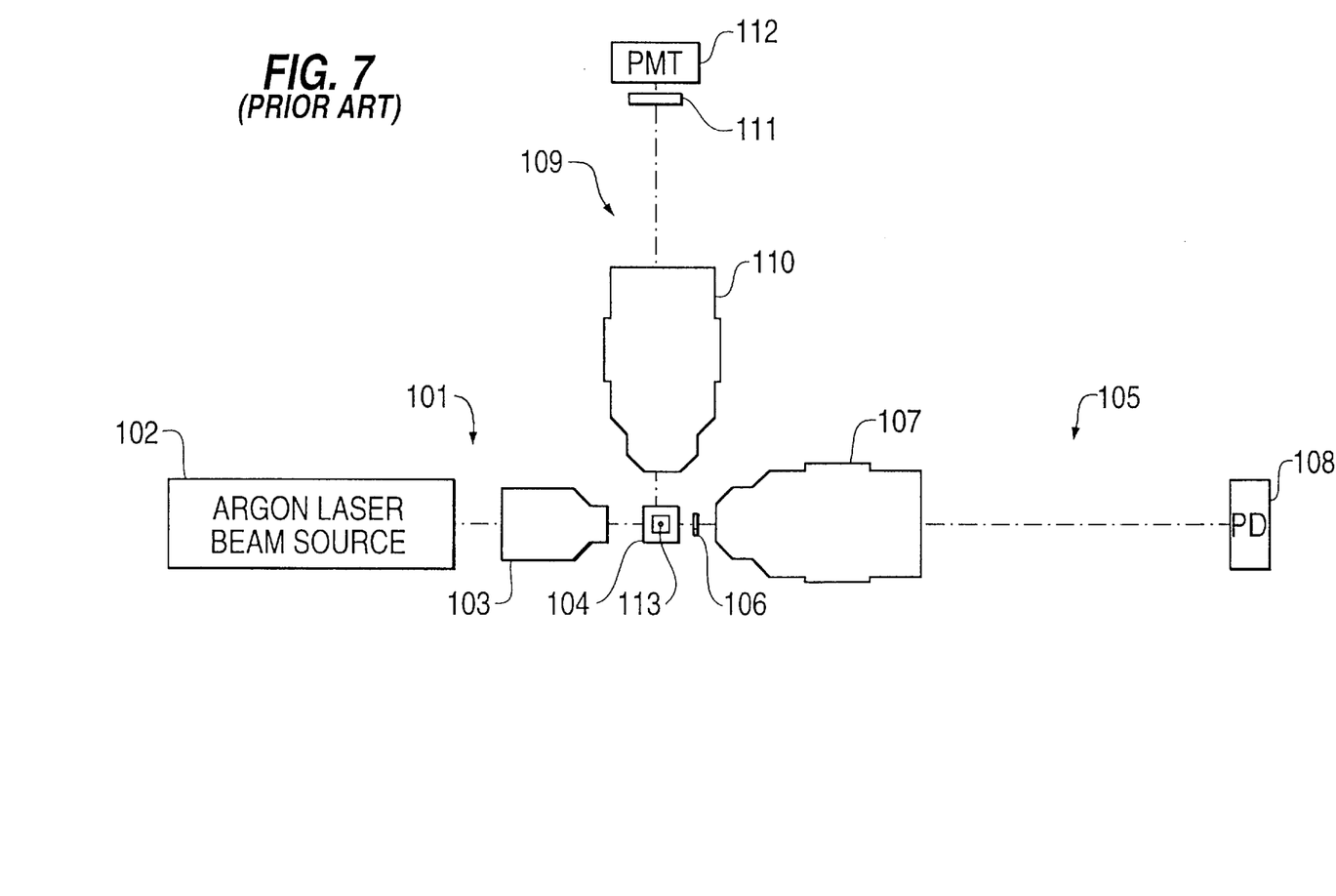
FIG. 7 is a schematic explanatory drawing showing a structure of a detecting section of a prior art flow cytometer.

Hitherto, a flow cytometer has been known widely as an apparatus for analyzing particles. FIG. 7 shows a detecting section of a typical prior art flow cytometer.

In FIG. 7, a sheathed sample flow containing particulate components such as blood corpuscles and various cells is formed in a flow cell 104 by surrounding the sample with a sheath solution as an outer layer thereof (the particulate components and the fluid flow in a direction vertical to the page). An irradiating optical system 101 comprises an argon laser beam source 102 and a condenser lens unit 103. Light output from the irradiating optical system 101 is irradiated to a sheathed sample flow 113 formed in the front flow cell 104.

A front light receiving optical system 105 for receiving light emitted in the front direction from the sheathed sample flow 113 in the flow cell 104 comprises a beam stopper 106, an objective lens unit 107 and a photodiode 108. The beam stopper 106 blocks front direct light which is output from the argon laser beam source 102 and transmits through the flow cell 104 in the front direction. The objective lens unit 107 detects scattered light and fluorescent light (front scattered light and front fluorescent light) emitted in the front direction from the sheathed sample flow 113 in the flow cell 104. The photodiode 108 detects the front fluorescent light which has passed through the objective lens unit 107.

A side light receiving optical system 109 for receiving light emitted in the side direction from the sheathed sample flow 113 in the flow cell 104 comprises an objective lens unit 110, a sharp-cut filter 111 and a photo-multiplier 112. The objective lens unit 110 detects scattered light and fluorescent light (side scattered light and side fluorescent light) emitted in the side direction from the sheathed sample flow 113 in the flow cell 104. The photo-multiplier 112 detects the side fluorescent light which has passed through the object lens unit 110 and the filter 111.

It has been known to use rod lenses instead of the objective lens units 107 and 110 in order to miniaturize and simplify the detecting section of such typical flow cytometer as disclosed in (a) Japanese Patent Publication No. Hei. 5-48413 ("Flow Cell for Measuring Specimen") and (b) Japanese Utility Model Laid-Open No. 60-176163 ("Sheath Flow Cell Apparatus") for example.

A rod lens is a lens whose shape is cylindrical and whose refractive index is distributed so as to change parabolically and continuously from a center axis of the cylindrical lens to a peripheral surface thereof. It is called also as an index distributed lens, a distributed index lens or a SELFOC lens. When such rod lens is employed, light incident to one end surface (flat face) of the rod lens propagates through the cylinder while describing a sine curve or helical optical path and is output from the other end surface (flat face).

It is advantageous in general if a light condensing ability could be improved or the restriction on the optical configuration be relaxed in the flow cytometer. For example, both the flow cell for measuring specimen in the above-mentioned publication (a) and the sheath flow cell apparatus in (b) have realized the miniaturization and simplification of the detecting section by embedding the rod lens into the flow cell to shorten a distance from an object (sheathed sample flow) to the lens's entrance surface in order to compensate the small numerical aperture of the lens.

However, while the end surface of the rod lens contacts with fluid (reagent) flowing through the flow cell in the flow cell for measuring specimen in the above-mentioned publication (a), there is the possibility of deteriorating optical characteristics of the rod lens in a long run because the reagent may contain a surface active agent and chemicals which exert ill effects on elements realizing the distributed index of the rod lens. Even if the end surface of the rod lens is coated with a thin film, it is difficult to maintain its chemical resistance for a long period of time. Further, although a hole is perforated through a wall face of the flow cell in the sheath flow cell apparatus of the above-mentioned publication (b), it is difficult to optically grind the inner wall of the hole. Even if an optical adhesive is filled into the hole, it causes a problem that a light transmitivity to the rod lens drops.

SUMMARY OF THE INVENTION

Accordingly, in view of such problems, it is a primary object of the present invention to provide a particle analyzer which can maintain optical characteristics of an optical system which is one component thereof at a fixed level for a long period of time.

In order to achieve the aforementioned object, according to the present invention, there is provided a particle analyzer comprising a flow cell for forming a sheathed sample flow containing particulate components; an irradiating optical system for irradiating a sheathed sample flow formed in the flow cell; and a light receiving optical system for receiving light emitted from the sheathed sample flow of the flow cell irradiated by the irradiating optical system; wherein the light receiving optical system comprises a rod lens to which the light emitted from the sheathed sample flow in the flow cell enters and an entrance surface of the rod lens is curved.

A known flow cell for forming a sheathed sample flow containing particulate components such as blood corpuscles and various cells may be used for the flow cell. By using such flow cell, the sheathed sample flow is formed by sheathing the sample with a sheath solution as an outer layer. A known irradiating optical system comprising an argon laser beam source and a condenser lens unit for example may be used for the irradiating optical system. The sheathed sample flow in the flow cell is irradiated by such irradiating optical system.

The light receiving optical system receives light emitted from the sheathed sample flow in the flow cell irradiated by the irradiating optical system to detect desired scattered light and fluorescent light. This light receiving optical system is disposed at a predetermined place corresponding to the purpose of detection. That is, when it is to be used as a front light receiving optical system for receiving light emitted in the front direction from the sheathed sample flow in the flow cell, it is disposed in front of the sheathed sample flow in the flow cell. When it is to be used as a side light receiving optical system for receiving light emitted in the side direction from the sheathed sample flow in the flow cell, it is disposed on the side of the sheathed sample flow in the flow cell. Finally when it is to be used as the front and side light receiving optical systems, it is disposed in front of and on the side of t sheathed sample flow in the flow cell.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE PREFERRED EMBODIMENTS

The light receiving optical system includes a rod lens to which the light emitted from the sheathed sample flow in the flow cell enters. A lens 1 to 2 mm in diameter and 3 to 30 mm in length is used for the rod lens. One end surface (end surface close to the flow cell) which is an entrance surface of the rod lens is curved. Such entrance surface allows a numerical aperture to be increased as compared to a rod lens having a flat entrance surface, even if it has the same material and same diameter.

The entrance surface may be spherical or aspherical. Further, it may be convex or concave. When it has a convex face, such merits are brought about that both the numerical aperture and light condensing ability increase, improving S/N ratio of signals to be detected. It is noted that the other end surface which is an exit surface of the rod lens may be curved or flat.

When the light receiving optical system is used as the front light receiving optical system or as the side light receiving optical system and the front light receiving optical system, it is preferable for the rod lens of respective front light receiving optical systems to be equipped with the beam stopper on the entrance surface thereof for blocking front direct light from the irradiating optical system.

The beam stopper on the entrance surface is formed by using a high precision masking technology in IC fabrication processes. That is, it is formed by evaporating an IC masking material such as Cr, Au—Cr, Au or the like on the entrance surface of the rod lens. The shape of the beam stopper may be arbitrarily set corresponding to its purpose, like linear (one-dimensional shape) or in plane (two-dimensional shape). Further, it is preferable to cut part of the entrance surface of the rod lens into a V-shaped groove and to mask so as to cover the groove portion. Thereby, a double structure by which light is reflected both by the surface of the groove and by the surface of the mask may be realized.

If the rod lens is equipped with the beam stopper on its entrance surface, no beam stopper and its micro-adjustment mechanism need to be provided separately. Accordingly, it allows intended light other than the direct light to be received preferentially and at the same time, the optical system to be simplified and miniaturized.

Preferably, the rod lens in the light receiving optical system is integrally equipped with a wavelength selection filter. That is, they are integrated so as to be able to handle the lens and filter as one part by forming a filtering member on the surface of the lens, by bonding the lens and the filtering member or by composing the lens itself by the filtering member. The particle analyzer may be miniaturized and simplified by providing a filtering function to the rod lens itself, differing from the prior art particle analyzer in which the wavelength selection filter and the lens unit are provided separately.

The above and other advantages of the invention will become more apparent in the following description and the accompanying drawings.

[Concrete Embodiments of the Invention]

Five embodiments of the present invention will be explained in detail below with reference to the drawings. It is noted that the present invention is not confined only to these embodiments.

The inventor et al. have started with understanding of basic characteristics of a rod lens before using it to a particle analyzer, and so part thereof will now be explained. It is noted that a concrete calculating method will be omitted and only results thereof will be explained here because it might otherwise become redundant to explain it.

Figure 13:
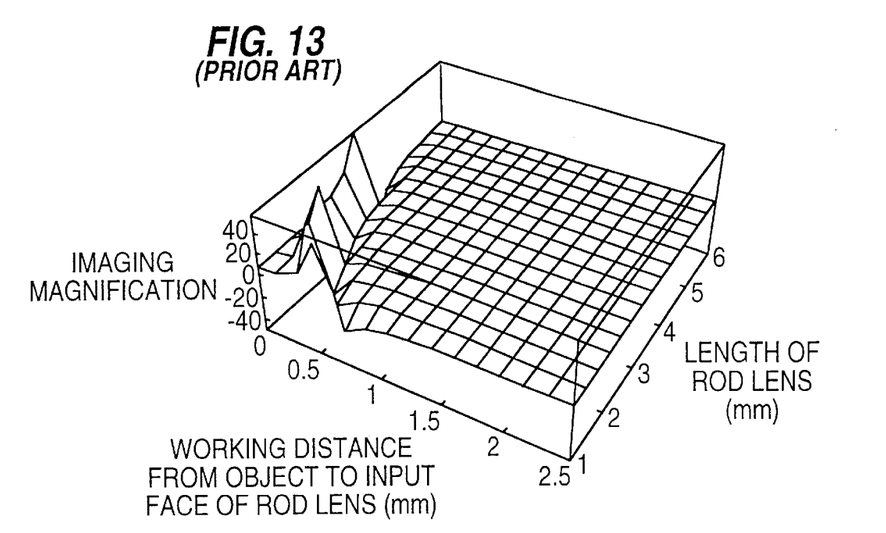
FIG. 13 is an explanatory diagram showing an imaging magnification of the rod lens whose entrance surface is ground flatly and which is used in the detecting section of the prior art flow cytometer.
Figure 14:
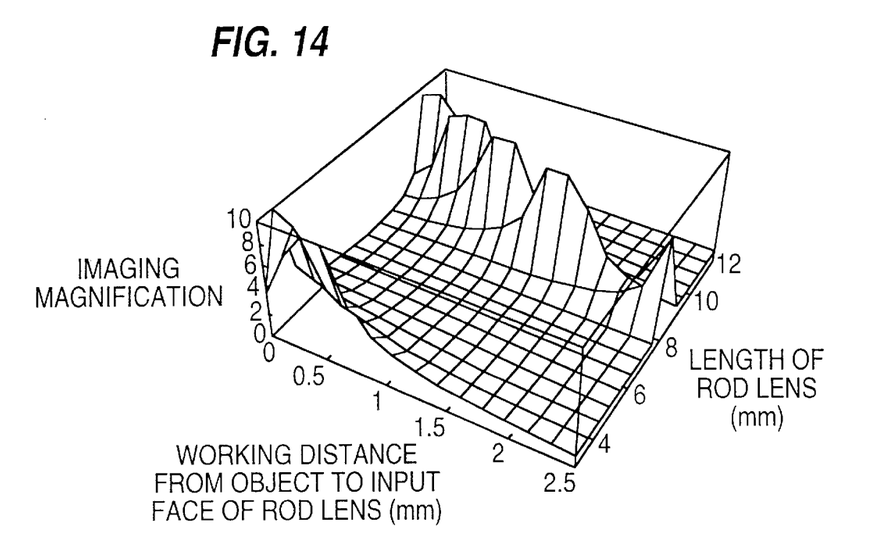
FIG. 14 is an explanatory diagram showing an imaging magnification of the rod lens whose entrance surface is ground spherically so that a radius of the sphere is 6.0 mm and which is used in the detecting section of the flow cytometer of the embodiments of the present invention.
Figure 15:
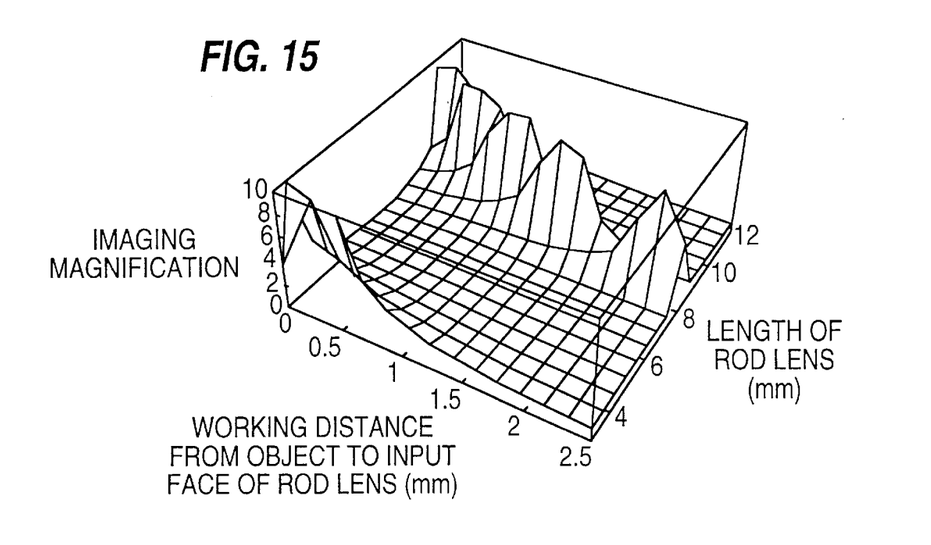
FIG. 15 is an explanatory diagram showing an imaging magnification of the rod lens whose entrance surface is ground spherically so that a radius of the sphere is 4.0 mm and which is used in the detecting section of the flow cytometer of the embodiments of the present invention.
Figure 16:
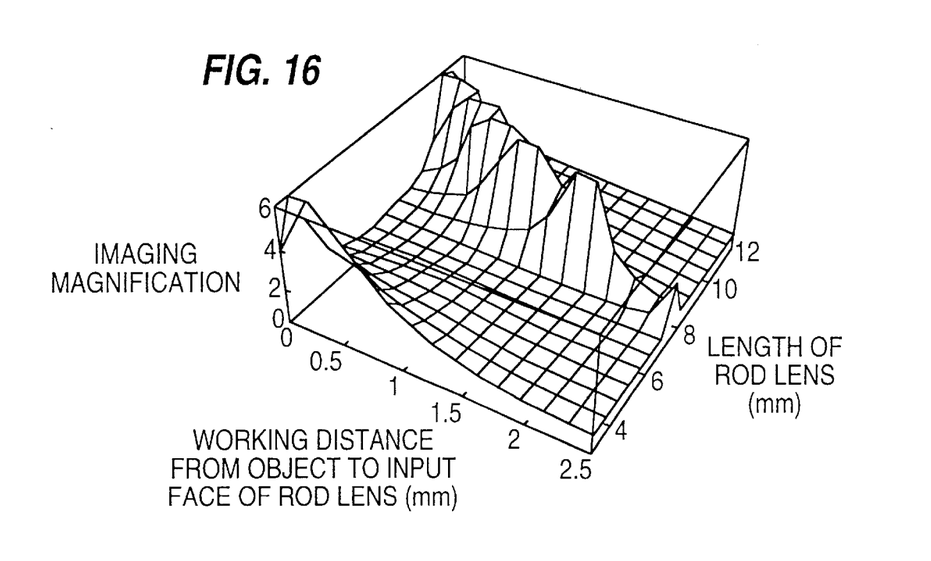
FIG. 16 is an explanatory diagram showing an imaging magnification of the rod lens whose entrance surface is ground spherically so that a radius of the sphere is 2.0 mm and which is used in the detecting section of the flow cytometer of the embodiments of the present invention.

FIGS. 13 through 16 show numerically calculated imaging magnifications of SML (SELFOC Micro Lens) H18, manufactured by Nippon Sheet Glass Co., Ltd., ground in predetermined manners. That is, FIG. 13 shows an imaging magnification of the H18 when its entrance surface is ground flatly. FIGS. 14 through 16 show imaging magnifications of the H18 whose entrance surface is ground spherically so that the radius of each sphere turns out as R=6.0 mm (FIG. 14), 4.0 mm (FIG. 15) and 2.0 mm (FIG. 16).

It has been found from these simulation results that a working distance necessary for obtaining a certain magnification required to a flow cytometer, i.e. a distance from an object to the entrance surface of the rod lens, may be increased when the entrance surface of the rod lens is ground spherically. When a relationship between an effective numerical aperture of the rod lens and the working distance was studied by supposing particles within a flow path of a flow cell as the object and a distance from an outer wall surface of the flow cell to an edge of the rod lens as the working distance, it has been also found that the greater the working distance, the less the effective numerical aperture of the rod lens becomes and that the working distance may be increased while keeping the same effective numerical aperture by grinding the entrance surface of the rod lens spherically. Undergoing such basic studies, the inventor et al. have started to construct a flow cytometer concretely.

[First Embodiment]

Figure 1:
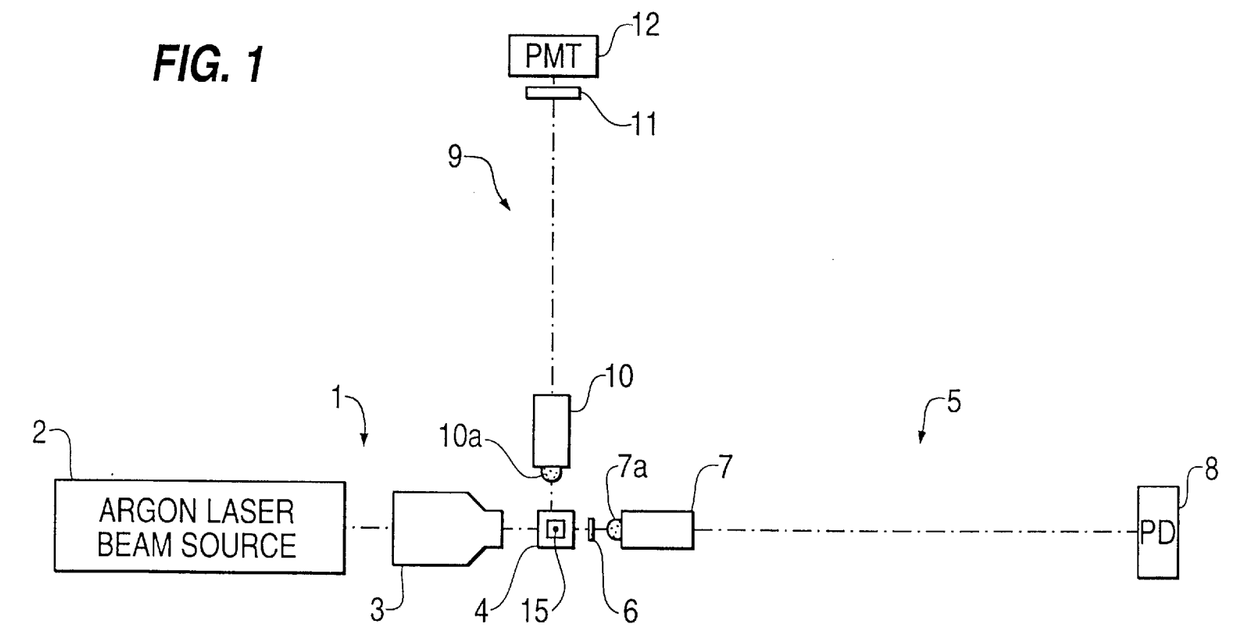
FIG. 1 is a schematic explanatory drawing showing a structure of a detecting section of a flow cytometer according to a first embodiment of the present invention.

FIG. 1 shows a detecting section of the flow cytometer as a particle analyzer according to a first embodiment of the present invention.

In FIG. 1, an irradiating optical system 1 includes an argon laser beam source 2 and a condenser lens unit 3. Light output from the irradiating optical system 1 is directed to a front flow cell 4. A sheathed sample flow 15 is formed in the flow cell 4 by sheathing a sample containing particulate components such as blood corpuscles and various cells with a sheath solution as an outer layer thereof (the particulate components and the fluid flow in a direction vertical to the page).

A front light receiving optical system 5 for receiving light emitted in the front direction from the sheathed sample flow 15 in the flow cell 4 comprises a beam stopper 6, a rod lens unit 7 and a photodiode 8. The beam stopper 6 blocks front direct light which is output from the argon laser beam source 2 and transmits through the flow cell 4 in the front direction. The rod lens unit 7 detects scattered light and fluorescent light (front scattered light and front fluorescent light) emitted in the front direction from the sheathed sample flow 15 in the flow cell 4. The photodiode 8 detects the front fluorescent light which has passed through the rod lens unit 7.

A side light receiving optical system 9 for receiving light emitted in the side direction from the sheathed sample flow 15 in the flow cell 4 includes a rod lens unit 10, a sharp-cut filter 11 as a wavelength selecting filter and a photo-multiplier 12. The rod lens unit 10 detects scattered light and fluorescent light (side scattered light and side fluorescent light) emitted in the side direction from the sheathed sample flow 15 in the flow cell 4. The photo-multiplier 12 detects the side fluorescent light which has passed through the rod lens unit 10 and the filter 11.

Figure 2:
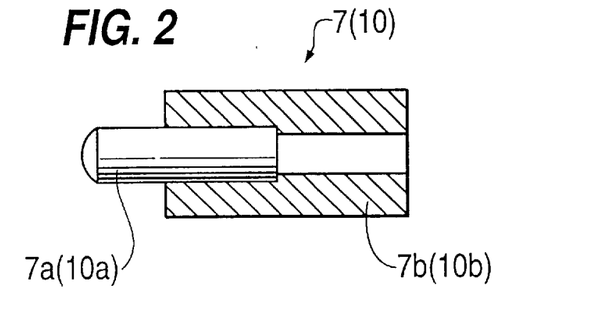
FIG. 2 is an explanatory drawing showing an enlarged structure of a rod lens in the detecting section of the flow cytometer in FIG. 1.

FIG. 2 is an enlarged view of each of the rod lenses 7 and 10 comprising a rod lens 7a (10a) fabricated by grinding the SML H18 manufactured by Nippon Sheet Glass Co., Ltd. and a cylindrical member 7b (10b) to which part of the rod lens 7a (10a) is inserted and is held by adhering by glass soldering. The rod lens 7a (10a) has a cylindrical shape with 1.8 mm in diameter and 10.0 mm in length whose one end surface (closer to the flow cell), i.e. an entrance surface, is spherical with 2.0 mm in radius.

Figure 8:
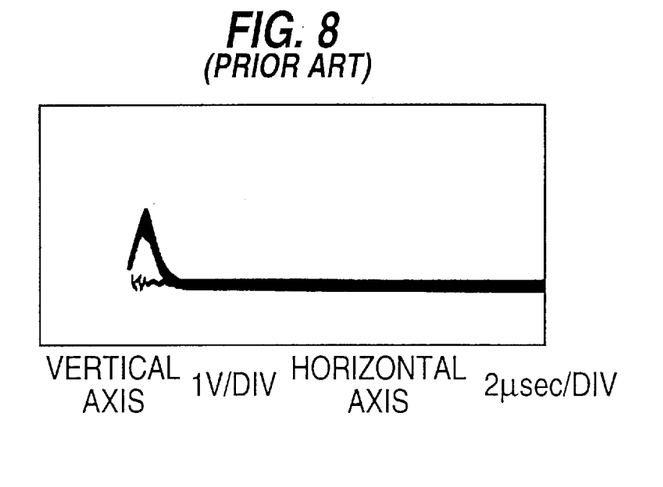
FIG. 8 is an explanatory graph showing an output of side fluorescent light when it is detected by an objective lens unit used in the detecting section of the prior art flow cytometer.
Figure 9:
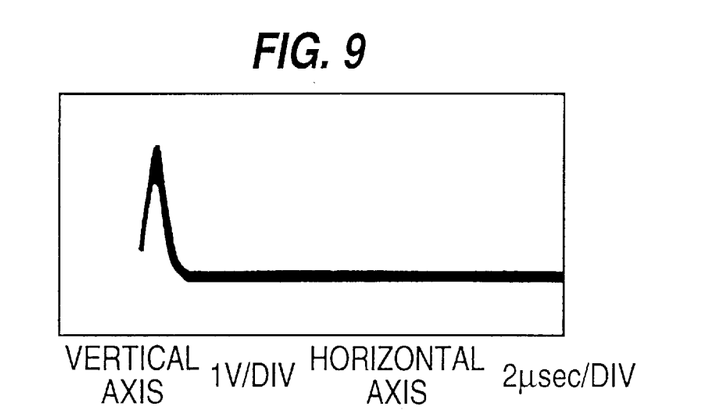
FIG. 9 is an explanatory graph showing an output of side fluorescent light when it is detected by the rod lens used in the detecting section of the flow cytometer of the first embodiment of the present invention.

FIGS. 8 and 9 show waveforms of side scattered light signals detected when latex particles 7 μm in diameter to which fluorescent dye is attached are supplied into the flow cell as particles to be studied respectively in the prior art flow cytometer equipped with the objective lens unit 110 and the flow cytometer of the first embodiment of the present invention equipped with the rod lens unit 10 having an equal numerical aperture with the objective lens unit 110. As it is apparent by comparing them, a signal which is about twice of that of the prior art (FIG. 8) is detected in the first embodiment (FIG. 9). This happens because of a difference of substantial light condensing abilities of the lenses. Generally, the objective lens is composed of many lenses and as the number of lenses increases, reflection on the surface of the lenses accumulate, thus dropping its transmission efficiency. The rod lens 7a (10a) which will do just by one lens is effective also in this point.

Figure 10:
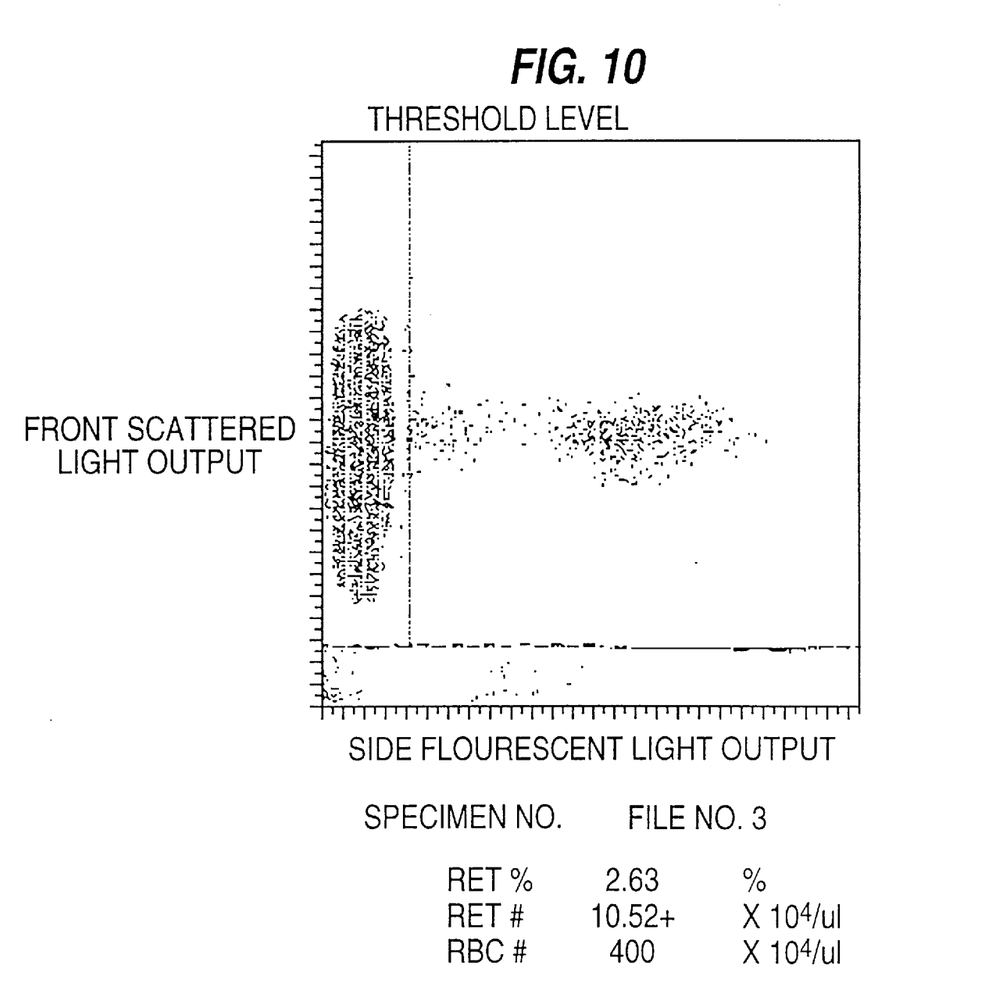
FIG. 10 is an explanatory graph showing a scattergram of the rod lens used in the detecting section of the flow cytometer of the first embodiment of the present invention.

FIG. 10 shows a scattergram taken by arranging the apparatus to measure reticulocyte adjusting particles (RETCHECK®, manufactured by Toa Medical Electronics Co., Ltd.). When the prior art apparatus and the inventive apparatus of the first embodiment were compared concerning to the distribution modes of the scattergrams and RET # (number of reticulocytes) and RET % (ratio of reticulocytes) which are counted results, it was found that there is no problem with the apparatus of the first embodiment and that it is possible to replace the prior art objective lens with the rod lens.

[Second Embodiment]

Figure 3:
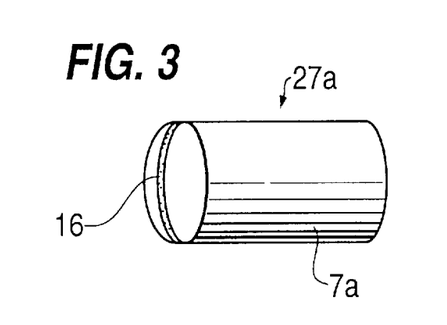
FIG. 3 is an enlarged perspective view showing a rod lens in a front light receiving optical system in the detecting section of the flow cytometer according to a second embodiment of the present invention.

FIG. 3 shows a rod lens 27a in which a linear beam stopper 16 of 100 to 200 μm in width is formed on the spherical entrance surface of the rod lens 7a so as to cross a vertex thereof, instead of the rod lens 7a in the first embodiment. The beam stopper 16 is formed by using a high precision masking technique employed in IC fabrication processes. That is, it is formed by evaporating an IC masking material such as Cr, Au—Cr, Au or the like on the entrance surface of the rod lens 7a. Although the beam stopper 16 may be used generally with a light receiving lens other than the rod lens, the rod lens may be said to be advantageous as a lens for forming the beam stopper 16 because a precision of an outside dimension of the light receiving lens has to be good in terms of the fabrication process in order to form the beam stopper 16 in high precision.

[Third Embodiment]

Figure 4:
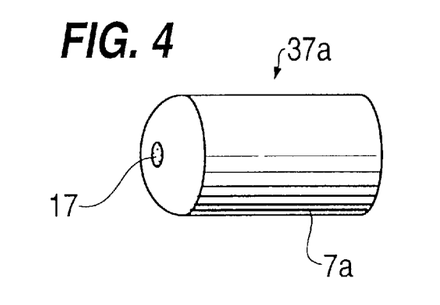
FIG. 4 is an enlarged perspective view showing a rod lens in the front light receiving optical system in the detecting section of the flow cytometer according to a third embodiment of the present invention.

The shape of the beam stopper may be arbitrarily set. Although the beam stopper 16 in FIG. 3 is linear having 100 to 200 μm in width, the width may be varied from several tens μm to several hundreds μm depending on its purpose. Further, it is also possible to form it in plane (circular, elliptical or various polygons) at the vertex of the entrance surface of the rod lens 7a of the first embodiment like a beam stopper 17 on the rod lens 37a shown in FIG. 4.

[Fourth Embodiment]

Figure 5:
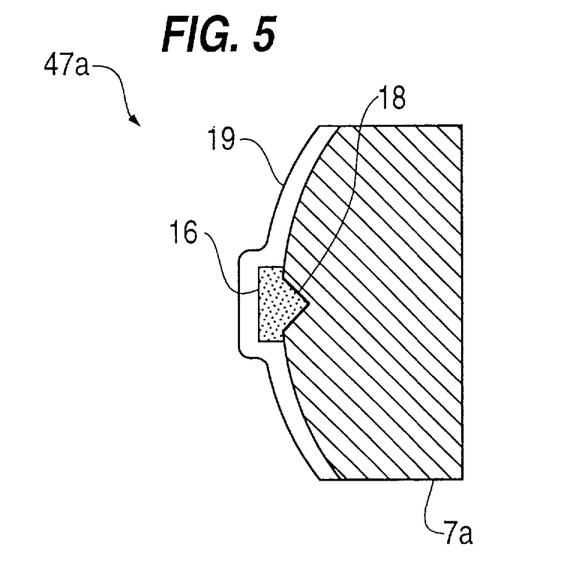
FIG. 5 is an enlarged longitudinal section view showing a rod lens in the front light receiving optical system in the detecting section of the flow cytometer according to a fourth embodiment of the present invention.

Preferably, the beam stopper 16 is formed by cutting a part of the entrance surface of the rod lens 7a of the first embodiment into a linear groove 18 having a V-shaped section and to mask so as to cover the groove 18 portion like a rod lens 47a shown in FIG. 5. It is because an ideal double structure may be formed by which, while most of light is reflected by the surface of the masking part, a very small amount of light which has transmitted through the masking portion is also reflected by the surface of the groove 18.

A process for fabricating it will be illustrated below. At first, ultrasonic wave is applied to the entrance surface of the rod lens 7a (cylinder 1.8 mm in diameter and 10.0 mm in length whose one end face, i.e. the entrance surface, is spherical with 2.0 mm in radius) to form the V-shaped groove 18 of 150 μm in width. Then, photoresist is applied to the whole entrance surface. A mask pattern in which a beam stopper of desired shape is patterned is placed on that and is exposed to ultraviolet rays to harden and solidify the photoresist film at the exposed portion. After that, part of the photoresist not exposed to the rays (a part which turns out to be the beam stopper 16) is removed by an organic solvent. Then, Cr is evaporated. Following to that, the remaining photoresist is removed by chemicals such as sulfuric acid+ hydrogen peroxide solution. Finally, an AR coating 19 is applied to the entire entrance surface.

Figure 11:
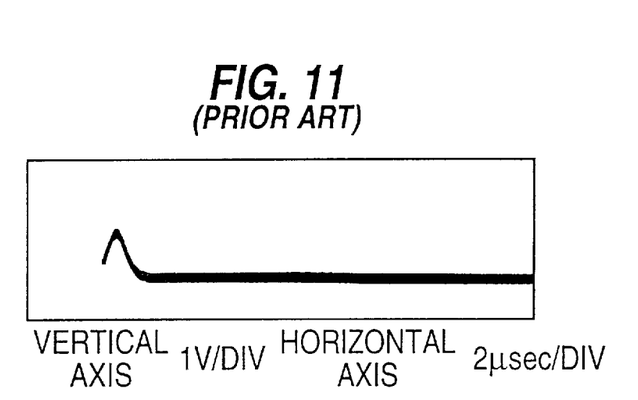
FIG. 11 is an explanatory graph showing an output of front scattered light when it is detected by a beam stopper and the objective lens unit used in the detecting section of the prior art flow cytometer.
Figure 12:
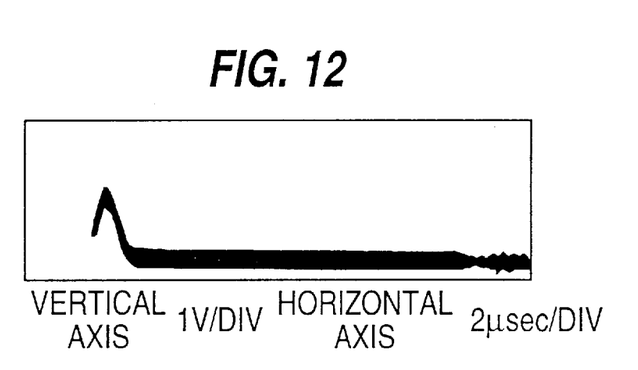
FIG. 12 is an explanatory graph showing an output of front scattered light when it is detected by the rod lens having a beam stopper used in the detecting section of the flow cytometer of the fourth embodiment of the present invention.

FIGS. 11 and 12 show waveforms of measured front scattered light from latex particles of 7 μm in diameter when the prior art flow cytometer shown in FIG. 7 and the flow cytometer of the fourth embodiment in which the rod lens 47a fabricated as described above is used instead of the beam stopper 6 and the rod lens 7a in FIG. 1 are used respectively for the front light receiving optical system. As it is apparent by comparing them, the one in the fourth embodiment of the present invention is detected as a signal which is about 1.5 times of that of the prior art.

[Fifth Embodiment]

Although the lens unit 110 and the filter 111 have been used separately in the detecting section of the prior art flow cytometer as shown in FIG. 7, the both are constructed integrally in a detecting section of the flow cytometer of the fifth embodiment to miniaturize and simplify it. That is, they are integrated so as to be able to handle the lens and filter as one part by coating a filtering member on the surface of the lens, by adhering the lens and the filtering member or by composing the lens itself by the filtering member.

Figure 6:
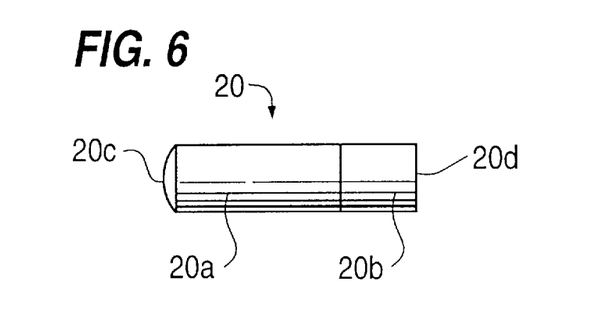
FIG. 6 is a an enlarged side view showing a rod lens in a side light receiving optical system in the detecting section of the flow cytometer according to a fifth embodiment of the present invention.

FIG. 6 shows one example thereof. A rod lens 20 is composed of a main body of the cylindrical rod lens 20a and a cylindrical colored glass 20b as a wavelength selection filter. An output face (right end surface) of the main body 20a is adhered optically with one end surface (left end surface) of the colored glass 20b. Further, the filtering member is coated on an entrance surface (left end surface) of the main body 20a to form an interference film 20c as a wavelength selection filter. An AR coating 20d is applied to an output face (right end surface) of the colored glass 20b.

When the rod lens 20 in FIG. 6 was used instead of the rod lens unit 10 and the filter 11 used in the side light receiving optical system 9 of the detecting section in the flow cytometer in FIG. 1 and when RETCHECK was measured in the same manner as described above, the same results with those described were obtained and it was confirmed that it causes no problem.

Thus, it is preferable to provide the rod lens 20 with the filtering function by itself. It is noted that the technological concept of providing the filter to the light receiving lens is applicable to lenses other than the rod lens as a matter of course and is applicable not only to the light receiving optical system but also to the irradiating optical system.

While the preferred embodiments have been described, variations thereto will occur to those skilled in the art within the scope of the present inventive concepts which are delineated by the following claims.

What is claimed is:

1. A particle analyzer, comprising:
   a flow cell for forming a sheathed sample flow containing particulate components;
   an irradiating optical system for irradiating said sheathed sample flow formed in said flow cell; and
   a light receiving optical system for receiving light emitted from said sheathed sample flow in said flow cell irradiated by said irradiating optical system, said light receiving optical system including a rod lens having a curved entrance surface, said rod lens being positioned outside said flow cell, said rod lens receiving the light emitted from said sheathed sample flow in said flow cell at said entrance surface.

2. The particle analyzer according to claim 1, wherein said entrance surface of said rod lens is spherical.

3. The particle analyzer according to claim 1, wherein said entrance surface of said rod lens is aspherical.

4. The particle analyzer according to claim 1, wherein said entrance surface of said rod lens is convex.

5. The particle analyzer according to claim 1, wherein said entrance surface of said rod lens is concave.

6. The particle analyzer according to claim 1, wherein said light receiving optical system includes a side light receiving optical system for receiving light emitted in the side direction from said sheathed sample flow in said flow cell.

7. The particle analyzer according to claim 1, wherein said light receiving optical system includes a front light receiving optical system for rejecting direct light among the light emitted from said irradiating optical system and for receiving light emitted in the front direction from said sheathed sample flow in said flow cell and said rod lens in said front light receiving optical system is equipped with a beam stopper on the entrance surface thereof for blocking the front direct light from said irradiating optical system.

8. The particle analyzer according to claim 7, wherein said beam stopper is a V-shaped groove.

9. The particle analyzer according to claim 7, wherein said beam stopper is formed by evaporating an IC masking material on the entrance surface of said rod lens.

10. The particle analyzer according to claim 1, wherein said rod lens of said light receiving optical system is integrally equipped with a wavelength selection filter.

11. The particle analyzer according to claim 10, wherein said wavelength selection filter is an interference film formed on the entrance surface of said rod lens.

12. A method for analyzing particles, comprising:

forming a sheathed sample flow containing particulate components;

irradiating the sheathed sample flow;

positioning a rod lens having a curved entrance surface outside the sheathed sample flow; and receiving light emitted from the sheathed sample flow irradiated by said irradiating step at said curved entrance surface of said rod lens.

13. The method according to claim 12, further comprising integrally providing a wavelength selection filter on the rod lens.

14. The method according to claim 12, further comprising integrally providing an interference film on the entrance surface of the rod lens.

15. The method according to claim 12, further comprising integrally providing a beam stopper for blocking light from said irradiating step on the rod lens.

16. The method according to claim 15, wherein said integrally providing step includes evaporating an IC masking material on the entrance surface of the rod lens.

17. The method according to claim 15, wherein said integrally providing step includes forming a V-shaped groove on the entrance surface of the rod lens.

* * * * *